United States Patent
Hasegawa et al.

(10) Patent No.: US 6,792,138 B2
(45) Date of Patent: Sep. 14, 2004

(54) METHOD OF FORMING AN IMAGE OF CILIUM AND CILIA

(75) Inventors: Naoki Hasegawa, Chofu (JP); Sayaka Konno, Hino (JP); Naruto Shinkai, Kawasaki (JP); Tomoya Kitano, Nagano (JP); Motoyasu Sagawa, Sendai (JP); Masami Sato, Sendai (JP); Akira Sakurada, Sendai (JP)

(73) Assignee: Olympus Optical Col., LTD, Tokyo (JP)

( * ) Notice: Subject to any disclaimer, the term of this patent is extended or adjusted under 35 U.S.C. 154(b) by 582 days.

(21) Appl. No.: 09/841,036

(22) Filed: Apr. 25, 2001

(65) Prior Publication Data

US 2001/0033679 A1 Oct. 25, 2001

(30) Foreign Application Priority Data

Apr. 25, 2000 (JP) ..................................... 2000-128968

(51) Int. Cl.$^7$ ............................................... G06K 9/00
(52) U.S. Cl. ....................................... 382/128; 600/160
(58) Field of Search .................................. 382/128, 133, 382/298; 348/65, 68, 69, 74, 77; 600/101, 109, 160, 168, 170, 171, 529

(56) References Cited

U.S. PATENT DOCUMENTS 5,107,845 A * 4/1992 Guern et al. ................ 128/664
6,139,860 A * 10/2000 Vinson ........................ 424/423
2004/0001662 A1 * 1/2004 Wong et al. ................... 385/15

OTHER PUBLICATIONS

Yi et al., "A New Method of Measuring Ciliary Beat Frequency Using Image Processing," *Proc. Int. Conf. of the IEE Engineering in Medicine and Biology Society*, Oct./Nov. 1996, pp. 680–681.*

Lamiot et al., "Video Image Analysis of Ciliary Activity of Human Respiratory Epithelium in Culture," *Proc. Int. Conf. of the IEEE Engineering in Medicine and Biology Society*, Nov. 1989, pp. 380–381.*

* cited by examiner

*Primary Examiner*—Andrew W. Johns
(74) *Attorney, Agent, or Firm*—Westerman, Hattori, Daniels & Adrian, LLP

(57) ABSTRACT

A method of forming an image of detailed cilium wrapped by mucus which exists in the epithelial layer of a cellular structure of a bronchus, where the method includes the steps of: irradiating an illumination light to the epithelial layer; generating Fresnel reflected light; irradiating the Fresnel reflected light to an image pick-up optical system; enlarging the Fresnel reflected light by the image pick-up optical system so that the enlarged Fresnel reflected light can be received by the image pick-up element; scanning at a velocity which is more than the velocity of motion of the cilium by the image pick-up element; transmitting image information from the image pick-up element to an observable medium with the naked eye; and displaying the image of detailed cilium by the observable medium.

15 Claims, 5 Drawing Sheets

(a)     (b)

(a)

(b)

METHOD OF FORMING AN IMAGE OF CILIUM AND CILIA

This application claims benefit of Japanese Application No. 2000-128968 filed on Apr. 25, 2000, the contents of which are incorporated by this reference.

FIELD OF THE INVENTION

This invention relates to a method of forming a detailed image of cilium and cilia which exists in an epithelial layer of a cellular structure of a bronchi or airway.

BACKGROUND OF THE INVENTION

As for mucociliary transport, ciliated epithelial cells play an important role as a barrier system for airway structures, such as bronchi or nasal cavities. The ciliated epithelial cells cover the surface of the bronchi. Thus, the abnormalities of ciliated epithelial cells cause various disorders of the trachea bronchial tree.

Ciliated epithelial cells are explained with reference to FIGS. 5 and 6. The cross-sectional view of a layer structure of a bronchial wall is shown in FIG. 5. Moreover, a partial cross-sectional view of a ciliated epithelial cells tissue is shown in FIG. 6.

As shown in FIG. 5, the bronchial wall consists of an epithelial layer 33 which has ciliated columnar epithelial cells 31 and a basement membrane 32, a subepithelial layer 35 which has bundles of elastic fibers 34, a muscle layer 37 which has a smooth muscle (bundle) 36, and an outer muscle layer 39 which is the outer layer of the bronchial wall. The cartilaginous layer 41 consists of cartilage 40, a pericartilaginous layer 42 and bronchial glands 38.

As shown in FIG. 6, the epithelial layer 33 consists of a basement membrane 32, ciliated columnar epithelial cells 31 and cilium 43, with the top of the epithelial layer 33 covered with the gel-like mucus 44. Ciliated columnar epithelial cells 31 are transparent cylinder shaped cells having a nucleus 45 and a length of about 100 $\mu$m. The ciliated columnar epithelial cells 32 exist on the basement membrane 32.

Cilium 43 is a colorless and transparent hair-like object with a diameter of 0.1–0.2 $\mu$m and length of several $\mu$m. Several hundred strands exist at the upper part of each ciliated columnar epithelial cell 31. The gel-like mucus 44 exists from the upper part of the ciliated columnar epithelial cells 31 extended upward by about 6 $\mu$m. Furthermore, the upper part of mucus 44 is solid-like. Cilium 43 performs the ciliary motion, a repeated transverse oscillation in the shape of a whip, in the gel-like mucus 44.

Since the epithelial layer 33 is transparent, when the bronchial epithelium of mucus in an organism is observed using an endoscope optical system, an illumination light permeates the cellular structure containing the epithelial layer 33 by about 0.5 mm. For this reason, the bundles of elastic fibers 34 which have color and exist in the cellular structure of a sublayer outside of the epithelial layer 33, are actually observed.

Apart from that, cilium disappears when a cell of bronchial epitheliums becomes cancerous. For this reason, the disappearance of cilium plays an important role in the evaluation of a malignant cell, and location of an affected region.

However, as mentioned above, since ciliated epithelial cells are transparent, it is hard in a conventional method to observe a disappearance of cilium in the process of the cells becoming cancerous, with the naked eye.

The following conventional methods have been used to observe cilia. There is the fluorescent method for observing with an endoscope, wherein an cellular organization extracted from an living body is dyed with a fluorescent paint and a laser light is irradiated onto the cellar organization. There is the method of observing a motion state more indirectly according to a change in the transmittance of a light and the measured frequency of the cilium. There is also the method of observing the scattered light of cilium by the transmitted illumination using a culture cell. In addition, there is the method of observing a change in the input-output signals using the light.

Currently, although it turns out that cilium disappears in the process of becoming cancer, changes in the form and the motion of the cilium caused by other diseases have not been clarified. This is because observation of cilium of a living tissue by the endoscope, etc. was difficult. If a change in the form or motion of cilium of and cilia a living tissue can be clearly discerned and data can be stored, such will become a great assistance in identifying or diagnosing diseases. This is not limited to the specialty of a bronchi or trachea bronchial tree but can also be applied to an otorhinilogy specialty and an obstetrics and gynecology specialty as well.

Moreover, although the observation of a change of the ciliary motion has only been performed in a culture cell, if a cilium observation by the naked eye of an in vivo becomes possible, it could not only confirm the effect of a medicine, but it could also contribute greatly to new medicine development in animal experiments.

Thus, when studying the relationship with a disease, it is important that the ciliary motion in the living body be observed as a direct image.

Conventionally, observing cilium in the living body with the naked eye has not been thought of at all, as mentioned above. In the conventional methods, a microscope, etc. was used to observe a partial cellular structure only after it was collected from an organism and moved to a receptacle so that the cilium of a cellular structure could be observed with the naked eye. However, according to the conventional methods, since the object was observed only about extremely limited parts, the exact range of a wide range observation and a disease could not be specified.

Moreover, since it is indispensable to collect the cellular structure which then becomes an observation object, the physical burden on a subject and the observer's operation burden becomes significant.

In view of the above mentioned problems inherent in the prior art, it is an object of the present invention to provide a method of forming an image of cilium and its motion in vivo, which can be observed with the naked eye.

SUMMARY OF THE INVENTION

Preferred embodiments of the present invention will now be described.

As mentioned above, in an endoscopic observation using any of the conventional observation procedures, the motion of cilium in vivo has not been confirmed with the naked eye.

In an observation screen, a white luminescent point like a halation may be visible accidentally. When it was observed that by raising the observation magnifying power stepwise about this white luminescent point, it has been confirmed that the white luminescent point part was shaking on and off at more than a predetermined magnifying power.

In the conventional observation, an observer had no idea that he was observing a luminescent point at all, since a white luminescent point is recognized as an obstacle to an observation of a subepithelial layer part, and the observation magnifying power in the endoscope was not high enough to confirm the shake of the luminescent point.

However, when this white luminescent point was observed by raising the magnifying power, it was confirmed that this white shake of a luminescent point was none other than the cilium and cilia with motions of the mucous membrane layer due to the motion of the cilia.

The confirmation of the motion of the cilium in vivo by the an endoscope was a very significant achievement scientifically because this was the first time ever that this has been accomplished.

Moreover, an animal and a person's extracted bronchi were observed by using a stereoscopic microscope. When a stereoscopic microscope was used, it was found that a higher magnifying power (500× on a 14 inch monitor) than that of an endoscope was needed in order to observe the cilium. Specifically, the structure (cilium) which by moving causes a halation has been confirmed by further enlarging the part which causes the halation during an animal experiment. In addition, the characteristics of periodicity and polarity were observed in the motion of this structure.

Therefore, cilium can be observed with the naked eye by irradiating illumination light so that a halation may be caused to the surface of ciliated epithelium, guiding the reflected light caused by the halation to an observation optical system, and enlarging the image of the light with a higher observation magnifying power than the predetermined magnifying power.

A method of forming an image of detailed cilium, according to the present invention, wrapped by mucus which exists in surface of epithelial layer of a cellular structure of a bronchus, wherein the method comprises the steps of: irradiating an illumination light to the epithelial layer; generating Fresnel reflected light; irradiating the Fresnel reflected light to an image pick-up optical system; enlarging the Fresnel reflected light by the image pick-up optical system so that the enlarged Fresnel reflected light is made to light-receive into an image pick-up element; scanning at a velocity which is more than the velocity of motion of the cilium by the image pick-up element; transmitting image information from the image pick-up element to an observable medium which can be observed with the naked eye; and displaying the image of detailed cilium and cilia by the observable medium.

Moreover, the step of irradiating an illumination light to the epitheliums layer includes a step of irradiating an illumination light from an upper part to the epithelial layer. In other words, it is not the permeation illumination from a back side but the reflective illumination from the upper part to the epithelial layer. When performing the permeation illumination from a back side with respect to the epithelial layer, it must illuminate from the exterior of an organ if it is performed in the living body, and the body surface must be cut open, and this is not realistic because a considerable burden is imposed on a the patient.

In addition, any type of monochromatic light or white light, may be used for an illumination light.

Moreover, the illumination procedure for creating the halation is as follows. Fresnel reflected light generated at the interface boundary between the cilium and the mucus, due to the difference of the refractive index therebetween, is utilized, and a motion state is observed based on the fluctuation of the reflected light by the ciliary motion.

When performing reflective illumination from the upper part with respect to the epithelial layer, in order to produce the Fresnel reflection broadly, the angle between the incident light of an illumination light and the direct reflected light reflected by the epithelial layer which irradiates to an image pick-up optical system is set to 45° or more (preferably 50°–70°).

Moreover, in order to obtain the angle between the incident and reflected light, the distance between an observed object and a surface of the image pick-up optical system on an observed object side which is proximate to the observed object is reduced and the inclination angle defined by an illumination optical axis and a reflected light axis is increased, simultaneously with the enlargement of a magnifying power, without changing a parallax of an illuminating system and an observation system. This is suitable when it is required that an outer diameter be small, like an endoscope.

Furthermore, in order to make the outer diameter small, a side-view endoscope can be used as the image pick-up optical system, and the step of irradiating an illumination light from an upper part to the epithelial layer comprises a step of arranging a radiation surface of an illuminating system in a direction where an irradiation angle with respect to the epithelial layer is inclined as much as possible, and the inclination angle between an illumination optical axis and a reflected light axis is increasing (axis of the side-view image pick-up optical system).

Moreover, in case of optical instruments, such as a microscope, with a comparatively large observation distance with respect to an observed object, it is preferable that the axis of an illuminating system is leaned with respect to the axis of an observation system. In this case, if the inclination of the axis of an illuminating system is made variable, it can be adjusted to the angle which tends to cause a Fresnel reflection in accordance with roughness of an observed object. This makes it possible for the inclination angle between the illumination optical axis and the axis of the image pick-up optical system to be variable. If an angle is made variable by the step of measuring an intensity of light which passes through the image pick-up optical system; judging an existence and a level of the Fresnel reflection based on the strength; and adjusting the inclination angle between the illumination optical axis and the axis of the image pick-up optical system, according to the judgment, the Fresnel reflection can be observed to a wide range so that a broad observation can be performed, and the exact range of a disease can be specified.

The step of scanning at a velocity which is more than the velocity of motion of the cilium by the image pick-up element includes a step of providing a high speed camera with the image pick-up element. The high speed camera is defined as that which can obtain an image of 100–10000 sheets per second.

The step of enlarging the Fresnel reflected light by the image pick-up optical system so that the enlarged Fresnel reflected light can be received by the image pick-up element includes a step of providing a high pixel and high resolution system with the image pick-up element. The image pick-up element of a high pixel and high resolution generally has 20–1,000,000 pixels, and more preferably it has more than a 1,000,000 pixels.

The medium which can observe the image by the image pick-up element with the naked eye includes a television monitor. If a television monitor has a common image pick-up element, a very general television monitor is sufficient. If the image pick-up elements are a high speed camera or a high pixel and high resolution system, it is desirable that a scanning speed is high and resolving power is excellent.

The medium observable with the naked eye includes an oscilloscope. On the basis of the electrical signal from the image pick-up element, the frequency of a motion of cilium may be observed not as an image but as a waveform with the naked eye.

When the medium observable with the naked eye includes a television monitor, a display magnifying power of the cilium is 70 magnifications or more.

Further, the method of forming an image of detailed cilium, according to the present invention, comprises a step of providing a recording apparatus for recording the image information simultaneously with the step of transmitting the image information from the image pick-up element to the observable medium with the naked eye. As the recording device, a digital camera, a film camera, a video tape and a video film, a waveform recording device, etc. can be applicable, so that it is convenient to compare a motion of various cilium.

DETAILED DESCRIPTION OF THE PREFERRED EMBODIMENT

Figure 1:
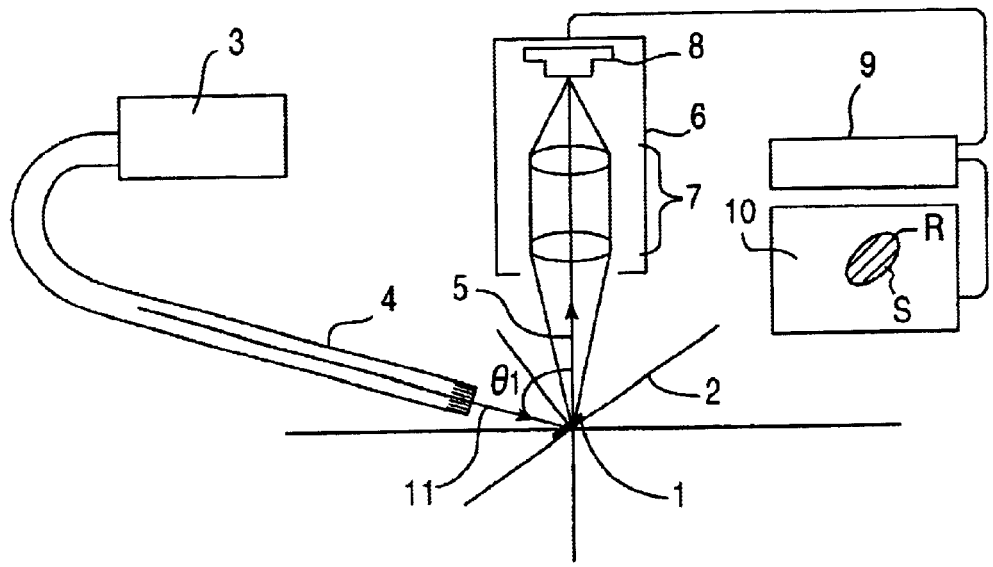
FIG. 1 is a diagram of the optical instruments used for observing cilium under the a microscope according to the first embodiment of the present invention.

FIG. 1 is a diagram of the optical instruments used for observing cilium according to the first embodiment of the present invention. In this embodiment, sample 1, such as the living tissue excised from the inside of the body, such as an animal, are fixed on a stage 2 having an adjustable inclination-angle.

A light is irradiated to the sample 1 through a fibre 4 from a light source 3, and a direct reflected light 5 reaches an image pick-up element 8 via an observation system 7 and a microscope 6. The observation system 7 includes an objective lens and an image formation lens. After performing a signal processing by a camera control unit 9, an image is output to a monitor 10.

In this case, by adjusting the inclination-angle of the fibre 4 and the stage 2, the angle of reflection, θ1 between an illumination light 11 and the direct reflected light 5, is adjusted. The angle of reflection θ1 is adjusted so that a Fresnel reflection at the cilium site of the sample 1 can be produced efficiently while observing the image on monitor 10. The illumination range of the illumination light 11 covers not only the intersection of the sample 1 and the observing system 7, but also all ranges to be observed.

In addition, in the adjusting method of the angle of reflection θ1, when a diseased part in the living body is observed directly without using the microscope 6, since there is no part corresponding to the stage 2, the radiation angle of the illumination light 11 is adjusted by changing the angle of reflection of the fibre 4.

Figure 2:
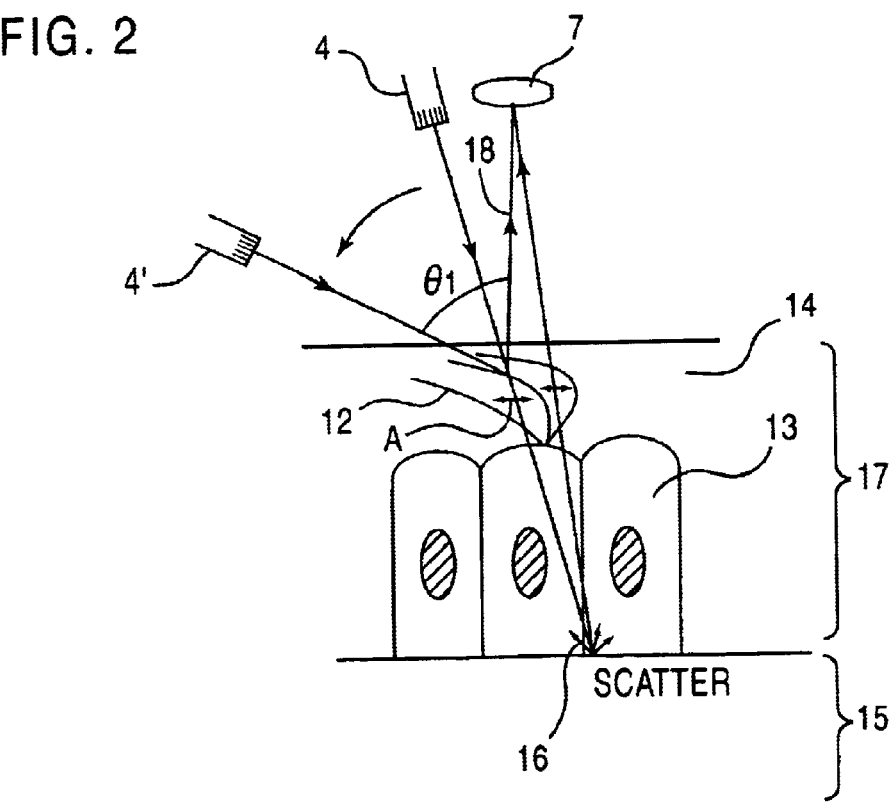
FIG. 2 is an explanatory drawing showing the reflective state of the light upon irradiating an illumination light to the cellular structure which has cilium, using the optical instrument of FIG. 1.

FIG. 2 is an explanatory drawing showing the reflective state of the light upon irradiating an illumination light to the cellular structure which has cilium 12, using the optical instruments of FIG. 1. The cilium 12 of a bronchus is formed on the upper part of an epithelial cell 13, and is covered with the mucus 14 and is oscillating so that a whip may be struck in the direction of arrow head A.

According to the observation method of the prior art, since the fibre 4 is positioned vertical with regard to the cellular organization, the illumination light passes through the cilium 12 and the epithelial cell 13 to reach a subepithelial layer 15, where the illumination light disperses and a portion of the dispersed light becomes incident on the observation system 7 so that the an observation image is obtained. In the case, the observation image is not of the cilium 12, but instead, the image of the epithelial cell 13.

The light 16, which is the illumination light scattered in the subepithelial layer 15 in the conventional observation, is observed through the observation system 7 as the image of the subepithelial layer 15.

On the other hand, since the cellular organization (epithelial layer 17) containing the cilium 12, above the subepithelial layer 15, is colorless and transparent, almost all of the illumination light from the fibre 4 permeates and is not observed.

In order to observe the cilium 12 covered with the colorless and transparent mucus 14, the refractive index difference of the mucus 14 and the cilium 12, is used to produce, in the interface boundary between the mucus 14 and the cilium 12, a Fresnel reflection, wherein the Fresnel reflected light generated is guided to the observation system 7 so it can be visualized. In order to strengthen the optical intensity of the Fresnel reflected light, the irradiation angle is made large with respect to the normal line of a reflective boundary surface.

For example, the illumination axis of the fibre 4 for the conventional observation state is leaned suitably to the inclined direction of fibre 4'. Then, the angle θ1 between the incident light and the direct reflected light 18 is made 45° or more so that the Fresnel reflected light 18 is produced. After photographing the reflected light 18 with the image pick-up element 8 of FIG. 1, through the observation system 7, and performing a signal processing by the camera control unit 9, an image is output to the monitor 10.

Herein, under the conditions of low magnifying power, where the direct reflected light 18 and the direct scattered light 16 are observed simultaneously, bright range R (see FIG. 1) by reflected light 18 is observed as if it caused by the halation partially on the image of a subepithelial layer 15.

In this case, boundary part S (see FIG. 1) of an observation image and a reflective image, strength of reflected light is usually changing by ciliary motion periodically.

Since the Example uses the change of this boundary part and was made to observe the change by the image, the existence of cilium is discriminable.

Figure 3:
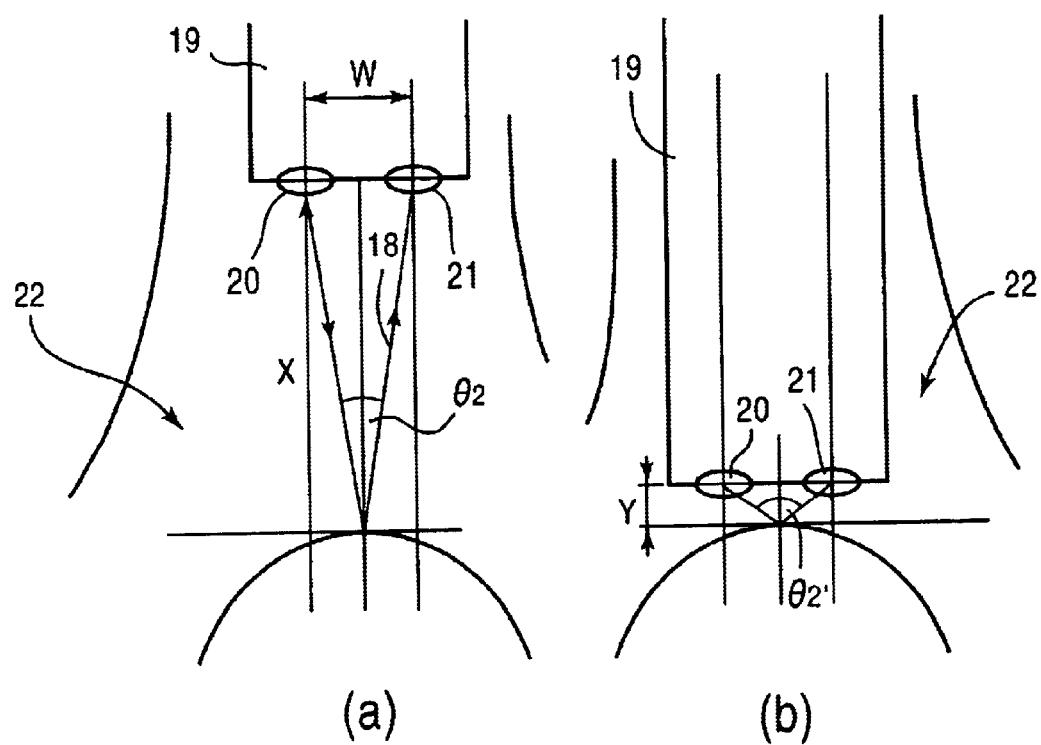
FIG. 3 is an explanatory drawing of a principal part of the lighting used for observing cilium under an endoscope according to a second embodiment of the present invention.

FIG. 3 is an explanatory drawing of a principal part of the lighting used for observing cilium under an endoscope according to a second embodiment of the present invention.

In this embodiment, an observation is conducted in the living body using the observation apparatus shown in FIGS. 3(c) and 3(b). More specifically, the observation apparatus includes an endoscope 19, an illuminating system 20, an observation system 21 and bronchus 22. In this embodiment, like the observation apparatus shown in FIG. 1, the reflected light from an observed object through the observation system of an endoscope is picked up by an image pick-up element. After performing a signal processing of the light by a camera control unit, an image signal is output to a monitor (not shown in FIG. 3).

The outer diameter for the insertion part of the endoscope can only be enlarged slightly, due to the narrow space of the observation site of the organism, such as a bronchus. The angle between the incident light and the direct light 18 cannot be extended, since parallax W can not be enlarged.

When observing under an endoscope in this embodiment, the angle between the incident light and the direct reflected light 18 can be extended from θ2 shown in FIG. 3(a) to θ2' shown in FIG. 3(b), using parallax W of the illuminating system 20 and the observation system 21.

Moreover, in order to observe the form and moving state of the cilium as mentioned above, the area which seems to produce the halation needs to be enlarged. That is, an observation magnifying power needs to be increased.

Realistically, the simplest method is shown in FIG. 3(b). If the distance between the observed object and the surface, proximate to the observed object, of an observation optical system is made small from X of FIG. 3(a) to Y of FIG. 3(b), without changing the parallax W of the illuminating system 20 and the observation system 21, the angle between the incident light and the direct reflected light 18, can be extended from θ2 to θ2', by fulfilling simultaneously the restrictions of parallax W and enlargement of the observation magnifying power.

Figure 4:
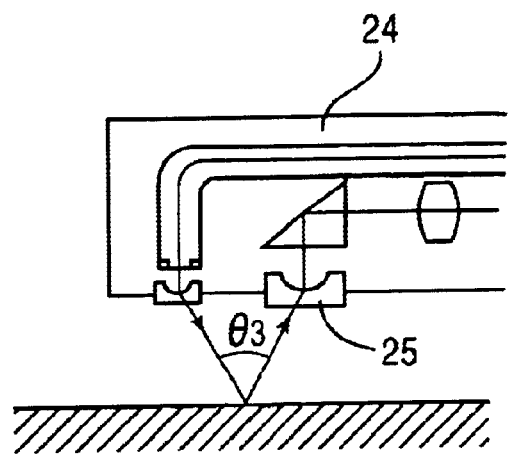
FIG. 4 is an explanatory drawing of a principal part of the lighting used for observing cilium under an endoscope according to a third embodiment of the present invention.
Figure 4:
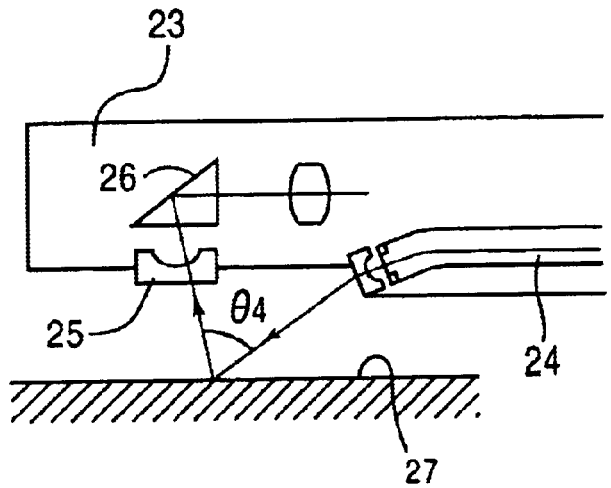
Figure 5:
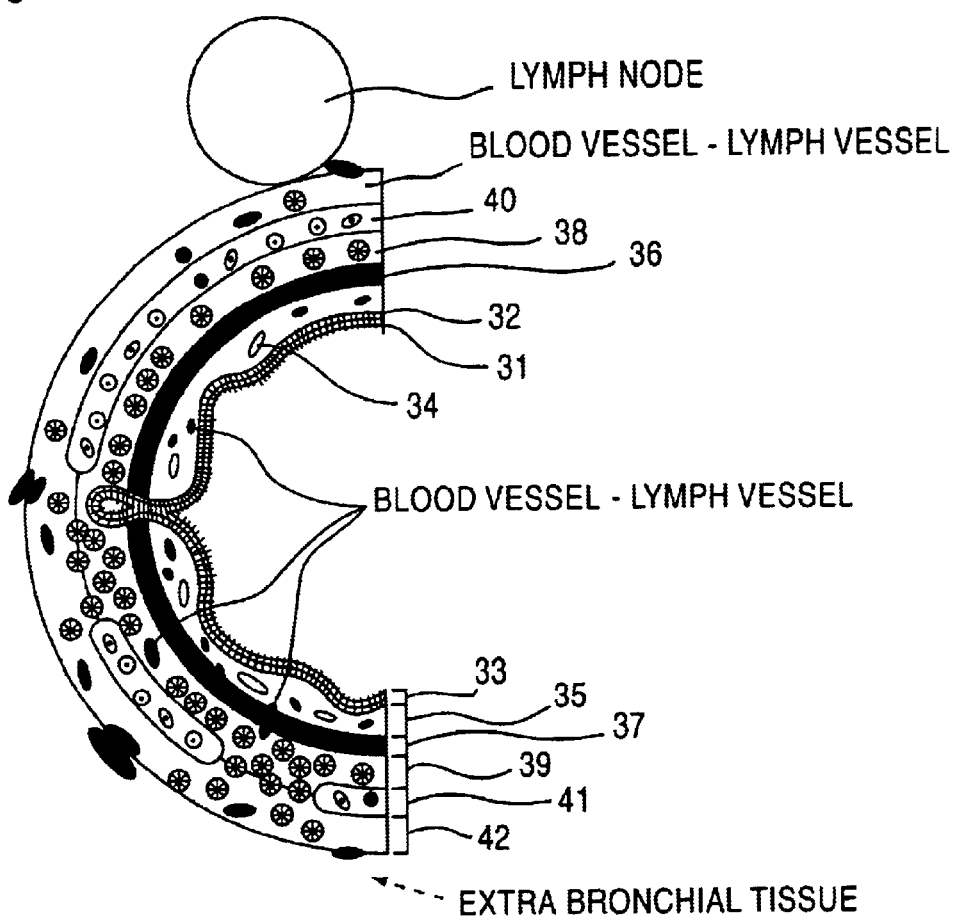
FIG. 5 is a partial cross-sectional view showing the layer structure of a bronchus wall.
Figure 6:
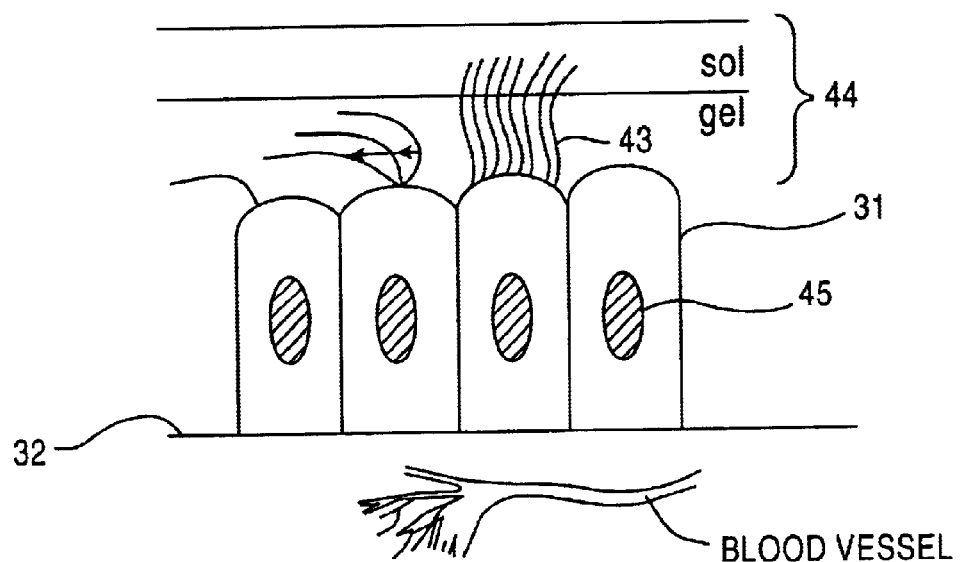
FIG. 6 is a partial cross-sectional chart of a ciliated epithelium cellular structure.

FIG. 4 is an explanatory drawing of a principal part of the lighting used for observing cilium under an endoscope according to a third embodiment of the present invention.

In this embodiment, an observation is conducted in the living body using the observation apparatus shown in FIGS. 4(a) and 4(b). More specifically, the observation apparatus includes a side-view endoscope 23, an illuminating system 24, an observation system 25, a prism 26 and the side wall of a bronchus 27.

In this embodiment, like the observation apparatus shown in FIG. 1, the reflected light from an observed object through the observation system of an endoscope is picked up by the pick-up element and is performed a signal processing by a camera control unit, an image signal is output to a monitor (not shown in FIG. 4).

When observing the cilium, which has long hair-like objects, in a side wall of a bronchus in a side direction, as shown in FIG. 4(a), the side-view endoscope 23 is used by converting the direction of the observation light via the observation system 25 and prism 26.

In the side-view endoscope 23, as illustrated in FIG. 4(b), the illuminating system 24 is constructed such that the angle between the incident light and the direct reflected light can be extended from θ3 to θ4. In order to construct the structure above, the plane of incidence of the observation system 25 and the radiation surface of the illuminating system 24 are disposed with a distance therebetween, and the direction of the radiation surface of the illuminating system 24 can be adjusted so that the direction of the irradiation angle to the side wall 27 of the bronchus, which is an observed object, is inclined as much as possible from the illuminating system 24.

Further, in each example, the reflected light from the cilium is received, while scanning at a velocity which is higher than a velocity of the cilium's motion by using a high speed camera etc, in order to grasp the ciliary movement visually.

Furthermore, from the range which caused the halation, in order to enable it to catch the form and the moving state of detailed cilium with the naked eye, the observation magnifying power is increased to 70 magnifications or more.

According to our experiment, when the display magnifying power is increased gradually, a satisfactory observation of the cilium can be performed if the display magnifying power is 70 magnifications or more. From the range which produces the halation, in order to grasp the form and the moving state of the detailed cilium with the naked eye, the observation magnifying power, which was conventionally about 20–30 magnifications, should be 70 magnifications or more. This observation magnification is defined by a photography magnification and a display magnification. For example, when setting the image pick-up magnification on an image pick-up element as 0.6 magnifications, the display magnification on the TV monitor of image information that was photographed with the image pick-up element is set to 124 magnifications with a 14 inch monitor.

In each example of this invention the cilium site of the observed object which the illumination light was irradiated, is observed in the state where a halation is produced, and signal processing such as enlargement are performed to image information light-received with the image pick-up element, and the form and the moving state of cilium are displayed on a monitor as an image.

Therefore, according to the method of each embodiment, the cilium can be observed not only in an excision tissue but in the living body with the naked eye. For this reason, a diagnosis of a pre-cancerous disease and the range of a disease can be specified. In addition, it can greatly contribute to the development of new medicine in animal experiments.

What is claimed is:

1. A method of forming an image of detailed cilium wrapped by mucus which exists in the epithelial layer of a cellular structure inside of a bronchus, the method comprising the steps of:

irradiating an illumination light to the epithelial layer from a direction inclined 45 degrees or more with respect to an optical axis of an image pick-up optical system;

generating a Fresnel reflected light according to a refractive index difference of between the mucus and the cilium;

irradiating the Fresnel reflected light as a halation light for the image pick-up optical system provided on an upper part of the epithelial layer;

enlarging the Fresnel reflected light by the image pick-up optical system;

scanning at a velocity which is more than the velocity of motion of the cilium and with resolving power by which the image pick-up element can recognize the cilium;

transmitting an electrical signal from the image pick-up element to a television monitor; and performing a scanning display at a velocity which is more than the velocity of motion of the cilium and with resolving power by which the television monitor can recognize the cilium.

2. A method of forming an image of detailed cilium wrapped by mucus which exists in the epitheliums layer of a cellular structure of a bronchus, the method comprising the steps of:

irradiating an illumination light to the epithelial layer;

generating a Frsnel reflected light;

irradiating the Fresnel reflected light to an image pick-up optical system;

enlarging the Fresnel reflected light by the image pick-up optical system;

scanning at a velocity which is more than the velocity of motion of the cilium by the image pick-up element;

transmitting image information from the image pick-up element to an observable medium which can be observed with the naked eye; and displaying the image of detailed cilium on the observable medium.

3. The method of forming an image of detailed cilium wrapped by mucus which exists in the epithelial layer of a cellular structure of a bronchus as recited in claim 2, wherein the step of irradiating an illumination light to the epithelial layer comprises a step of irradiating an illumination light from an upper part to the epithelial layer so that it is not the permeation illumination from a back side but the reflective illumination from the upper part of the epithelial layer.

4. The method of forming an image of detailed cilium wrapped by mucus which exists in the epithelial layer of a cellular structure of a bronchus as recited in claim 3, wherein the step of irradiating an illumination light from an upper part to the epithelial layer comprises step of irradiating an illumination light inclined 45 degrees or more with respect to an optical axis of the image pick-up optical system.

5. The method of forming an image of detailed cilium wrapped by mucus which exists in the epithelial layer of a cellular structure of a bronchus as recited in claim 3, wherein the step of irradiating an illumination light from an upper part to the epithelial layer comprises a step of irradiating an illumination light inclined 50–70° with respect to an optical axis of the image pick-up optical system.

6. The method of forming an image of detailed cilium wrapped by mucus which exists in the epithelial layer of a cellular structure of a bronchus as recited in claim 3, wherein the step of irradiating an illumination light from an upper part to the epithelial layer comprises a step of reducing a distance between the observed object and a surface of the image pick-up optical system on the observed object side which is proximate to the observed object, and increasing the inclination angle defined by an illumination optical axis and a reflected light axis, simultaneously with an enlargement of a the magnifying power, without changing a parallax of an illuminating system and an observation system.

7. The method of forming an image of detailed cilium wrapped by a mucus which exists in the epithelial layer of a cellular structure of a bronchus as recited in claim 3, wherein the image pick-up optical system is a side-view endoscope, and the step of irradiating an illumination light from an upper part to the epithelial layer comprises a step of arranging a radiation surface of an illuminating system in a direction where an irradiation angle with respect to the epithelial layer is inclined as much as possible, and the inclination angle between an illumination optical axis and a reflected light axis is increased.

8. The method of forming an image of detailed cilium wrapped by a mucus which exists in the epithelial layer of a cellular structure of a bronchus as recited in claims 4, 5, 6 or 7, further comprises a step of varying the inclination angle between the illumination optical axis and the axis of the image pick-up optical system.

9. The method of forming an image of detailed cilium wrapped by mucus which exists in the epithelial layer of a cellular structure of a bronchus as recited in claim 8, wherein the varying step comprises:

measuring the intensity of the light which passes through the image pick-up optical system;

judging an existence and a level of the Fresnel reflection based on the strength of the intensity; and adjusting the inclination angle between the illumination optical axis and the axis of the image pick-up optical system based on the judgment.

10. The method of forming an image of detailed cilium wrapped by mucus which exists in the epithelial layer of a cellular structure of a bronchus as recited in claim 2, wherein the step of scanning at a velocity which is more than the velocity of motion of the cilium by the image pick-up element includes a step of providing a high speed camera with the image pick-up element.

11. The method of forming an image of detailed cilium wrapped by mucus which exists in the epithelial layer of a cellular structure of a bronchus as recited in claim 2, wherein the step of enlarging the Fresnel reflected light by the image pick-up optical system includes a step of providing a high pixel and high resolution system with the image pick-up element.

12. The method of forming an image of detailed cilium wrapped by mucus which exists in the epithelial layer of a cellular structure of a bronchus as recited in claims 10 or 11, wherein the observable medium with the naked eye includes a television monitor.

13. The method of forming an image of detailed cilium wrapped by mucus which exists in the epithelial layer of a cellular structure of a bronchus as recited in claims 10 or 11, wherein the observable medium with the naked eye includes an oscilloscope.

14. The method of forming an image of detailed cilium wrapped by mucus which exists in the epithelial layer of a cellular structure of a bronchus as recited in claim 12, wherein when the observable medium with the naked eye includes a television monitor, a display magnifying power of the cilium is 70 magnifications or more.

15. The method of forming an image of detailed cilium wrapped by mucus which exists in the epithelial layer of a cellular structure of a bronchus as recited in claim 2, further comprises the step of providing a recording apparatus for recording the image information simultaneously with the step of transmitting the image information from the image pick-up element to the observable medium.

* * * * *